United States Patent [19]

Epstein et al.

[11] Patent Number: 5,594,027
[45] Date of Patent: Jan. 14, 1997

[54] AMINOCYCLOALKANOBENZODIOXOLES AS BETA-3 SELECTIVE ADRENERGIC AGENTS

[75] Inventors: Joseph W. Epstein; Gary H. Birnberg, both of Monroe; Gary E. Walker, Spring Valley; Minu D. Dutia, West Nyack; Jonathan D. Bloom, Hartsdale, all of N.Y.

[73] Assignee: American Cyanamid Company, Madison, N.J.

[21] Appl. No.: 435,469

[22] Filed: May 5, 1995

Related U.S. Application Data

[62] Division of Ser. No. 250,471, May 27, 1994, Pat. No. 5,510,376, which is a division of Ser. No. 10,973, Jan. 29, 1993, abandoned.

[51] Int. Cl.⁶ .................................................. A61K 31/36
[52] U.S. Cl. ............................................................. 514/463
[58] Field of Search ............................... 514/463; 549/433

[56] References Cited

U.S. PATENT DOCUMENTS 5,061,727  10/1991  Bloom et al. .

*Primary Examiner*—Nicky Chan
*Attorney, Agent, or Firm*—Hedman, Gibson & Costigan, P.C.

[57] ABSTRACT

The invention is antiobesity/antidiabetic/beta-3 agonists of the formula

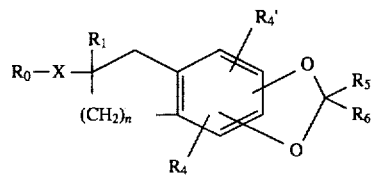

wherein the substituents $R_o$, $R_1$, $R_4$, $R_4'$, $R_5$, $R_6$ or n are as defined in the specification.

48 Claims, No Drawings

AMINOCYCLOALKANOBENZODIOXOLES AS BETA-3 SELECTIVE ADRENERGIC AGENTS

This is a divisional, of application Ser. No. 08/250,471, filed May 27, 1994 now U.S. Pat. No. 5,510,526; which is a divisional application of Ser. No. 08/010,973, filed Jan. 29, 1993, which is now abandoned.

BACKGROUND OF THE INVENTION

It is well known to employ medicinal agents in the treatment of persons suffering from diabetes, hyperglycemia and obesity.

Bloom et al., U.S. Pat. No. 5,061,727, discloses compounds having the general formula A:

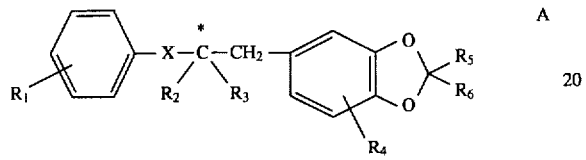

wherein $R_1$ and $R_4$ may be one or more groups which may be the same or different and are selected from the group consisting of hydrogen, $(C_1-C_4)$alkyl, $(C_1-C_4)$alkoxy, hydroxy, halogen, trifluoromethyl, carboxy, hydroxyalkyl, alkoxycarbonyl, $(C_1-C_4)$thioalkyl, sulfonyl and sulfinyl; X is a divalent radical consisting of

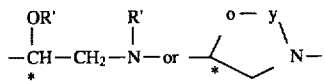

wherein R' is selected from the group consisting of hydrogen, $(C_1-C_4)$alkyl and $(C_1-C_4)$acyl and Y is selected from the group consisting of carbonyl and thiocarbonyl; $R_2$ and $R_3$ may be the same or different and are selected from the group consisting of hydrogen and $(C_1-C_4)$alkyl; $R_5$ and $R_6$ are selected from the group consisting of hydrogen, carboxy, alkoxycarbonyl, hydroxymethyl, —$CH_2OCH_2COOR_7$ and —$CH_2OCH_2CH_2OR_7$, where $R_7$ is hydrogen or $(C_1-C_4)$alkyl; with the provision that $R_5$ and $R_6$ may not both be hydrogen; which are useful in the treatment of diabetes, hyperglycemia and obesity; and which show a greater degree of selectivity for the $\beta_3$-adrenergic receptor than reference agents cited within the patent.

Cecchi et al., U.S. Pat. No. 4,707,497, discloses compounds having the general formula B:

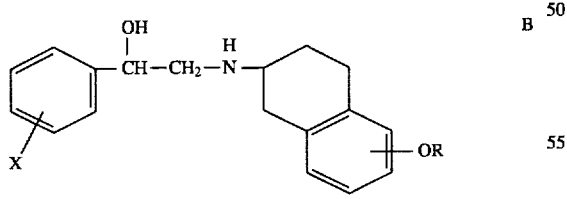

wherein X represents hydrogen, halogen, a trifluoromethyl or a lower alkyl and R represents hydrogen; a lower alkyl group not substituted, or substituted by a cycloalkyl group containing 3 to 7 carbon atoms, a hydroxyl group, a lower alkoxy, carboxy or lower carbalkoxy group; a cycloalkyl group containing 3 to 7 carbon atoms; or a lower alkanoyl group; or a pharmaceutically acceptable salt thereof; a process for its preparation; and pharmaceutical compositions containing it as active ingredient, useful for the treatment of obesity.

SUMMARY OF THE INVENTION

This invention is concerned with novel compounds of formula I:

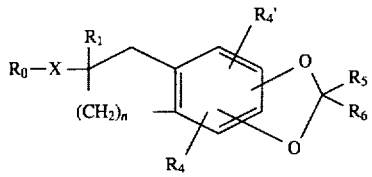

wherein:

$R_o$ may be

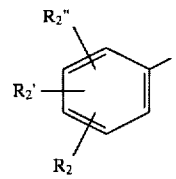

and $R_2$, $R_2'$ and $R_2''$ may be the same or different and are hydrogen, $(C_1-C_4)$alkyl, $(C_1-C_4)$alkoxy, hydroxy, halogen (chlorine, bromine, fluorine and iodine), trifluoromethyl, carboxy, hydroxy$(C_1-C_{10})$alkyl, $(C_1-C_{10})$alkoxycarbonyl, thio$(C_1-C_4)$alkyl, sulfonyl or sulfinyl;

or $R_o$ may be naphthyl, 5,6,7,8-tetrahydronaphth-(1 or 2-yl or 5,8-dihydronaphth-(1 or 2)-yl;

n is an integer from 1 to 3;

X is a divalent radical of

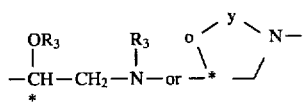

wherein $R_3$ is hydrogen, $(C_1-C_4)$alkyl, $(C_1-C_4)$acyl, $(C_1-C_4)$alkoxycarbonyl or benzoyl; Y is carbonyl or thiocarbonyl; $R_1$ is hydrogen or $(C_1-C_4)$alkyl; $R_4$ and $R_4'$ may be the same or different and are hydrogen, $(C_1-C_4)$alkyl, $(C_1-C_4)$alkoxy, hydroxy, halogen (chlorine, bromine, fluorine and iodine), trifluoromethyl, carboxy, hydroxy$(C_1-C_{10})$alkyl, $(C_1-C_{10})$alkoxycarbonyl, thio$(C_1-C_4)$alkyl, sulfonyl or sulfinyl;

$R_5$ and $R_6$ are hydrogen, carboxyl, $(C_1-C_4)$alkoxycarbonyl, hydroxymethyl, —$CH_2OCH_2COOR_7$ or —$CH_2OCH_2CH_2OR_7$, wherein $R_7$ is hydrogen, $(C_1-C_{10})$alkyl, or $CONHR_8$, $R_8$ is hydrogen, straight or branched $(C_1-C_{10})$alkyl or 2-methoxy-1-ethyl; with the proviso that $R_5$ and $R_6$ may not both be hydrogen; and the pharmacologically acceptable salts or esters thereof; the racemic mixtures thereof or the diastereomeric mixtures thereof.

The compounds of formula I have centers of asymmetry at the carbon atoms marked with an asterisk. The compounds may, therefore, exist in at least two and often four stereoisomeric forms. The present invention encompasses all stereoisomers of the compounds whether free from other stereoisomers or admixed with other stereoisomers in any proportion and thus included, for instance, racemic mixtures of enantiomers as well as the diastereomeric mixture of isomers. Preferably both asymmetric carbon atoms have the R absolute stereochemical configuration. The absolute configuration of any compound may be determined by conventional X-ray crystallography.

The preferred compounds are (R,R)-7-[5-(3-chlorophenyl)-2-oxo-3-oxazolidinyl]-7,8-dihydro-6H-indeno[4,5-d]-1,2-dioxole-2,2-dicarboxylic acid diethyl ester; (R,R)-7-[[2-(3-chlorophenyl)-2-hydroxyethyl]amino-7,8-dihydro-6H-indeno[4,5-d]-1,3-dioxole-2,2-dicarboxylic acid disodium salt; (R)-7-[[2-(3-chlorophenyl)-2-hydroxyethyl]amino-7,8-dihydro-6H-indeno-[5,6-d]-1,3-dioxole-2,2-dicarboxylic acid disodium salt; (R*,R*) and (R*,S*)-6-[5-(3-chlorophenyl)-2-oxo-3-oxazolidinyl]-5,6,7,8-tetrahydronaphtho[2,3-d]-1,3-dioxole-2,2-dicarboxylic acid diethyl ester; (R*,R*) and (R*,S*)-6-[[2-(3-chlorophenyl)-2-hydroxyethyl]-amino-5,6,7,8-tetrahydronaphtho[2,3-d]-1,3-dioxole-2,2-dicarboxylic acid disodium salt; (R*,R*) and (R*,S*)-6-[[2-(3-chlorophenyl)-2-hydroxyethyl]amino-4,5,6,7-tetrahydronaphtho[1,2-d]-1,3-dioxole-2,2-di-carboxylic acid disodium salt and the optically active derivatives thereof.

Also according to the present invention, there is provided a method of treating diabetes and/or hyperglycemia and/or obesity in humans or other mammals which comprises administering to a human or other mammal an antiobesity effective amount or an anti-hyperglycemia effective amount of a compound of the present invention.

Further, according to the present invention there are provided pharmaceutical compositions of matter comprising an effective amount of the compounds of the present invention in combination with a pharmaceutically acceptable carrier; as well as a method for increasing the content of lean meat in edible mammals, which comprises administering to edible mammals an effective amount of the compound. Also, the present invention provides processes for producing the compounds of the invention and a process for the resolution of the optical isomers of the invention and salts and ester thereof.

DETAILED DESCRIPTION OF THE INVENTION

The disease diabetes mellitus is characterized by metabolic defects in production and utilization of glucose which result in the failure to maintain appropriate blood sugar levels. The result of these defects is elevated blood glucose or hyperglycemia. Research on the treatment of diabetes has centered on attempts to normalize fasting and postprandial blood glucose levels. Treatments have included parenteral administration of exogenous insulin, oral administration of drugs and dietary therapies.

Two major forms of diabetes mellitus are now recognized. Type I diabetes, or insulin-dependant diabetes, is the result of an absolute deficiency of insulin, the hormone which regulates glucose utilization. Type II diabetes, or insulin-independent diabetes, often occurs in the face of normal, or even elevated levels of insulin and appears to be the result of the inability of tissues to respond appropriately to insulin. Most of the Type II diabetics are also obese.

Compounds of this invention induce lipolysis in rat adipocytes in a selective manner.

As effective hypoglycemic and weight loss agents, these compounds are useful for the treatment of hyperglycemia and obesity in Type II diabetes.

SELECTIVITY

β-Adrenergic receptors can be divided into $\beta_1$, $\beta_2$ and β3-subtypes. Activation of $\beta_1$-receptors invokes increases in heart rate while activation of $\beta_2$-receptors stimulates glycogen breakdown in muscle and thereby prevents glycogen synthesis. Activation of $\beta_3$-receptors stimulates lipolysis (the breakdown of adipose tissue triglycerides to glycerol and free fatty acids), and thereby promotes the loss of fat mass. Compounds that stimulate $\beta_3$-receptors will have antiobesity activity. In addition, they have hypoglycemic or anti-diabetic activity, but the mechanism of this effect is unknown. A compound that selectively stimulates $\beta_3$-receptors, i.e. has little or no $\beta_1$ or $\beta_2$-activity, will have the desired anti-diabetic and/or anti-obesity activity, but without the undesired effects of increased heart rate ($\beta_1$-effect) or muscle tremor ($\beta_2$-effect).

Selectivity of a compound is determined using the following procedures.

Binding assays for $\beta_1$-effect are carried out by the use of membranes from rat heart, and $\beta_2$-effect by the use of membranes from rat lung by the method described in Neve, et al., J. Pharmacol. Exp. Ther., 1985, 235, 657–664 with the following exceptions:

1. the incubation volume is 0.5 ml,
2. the incubation time is 1 hour,
3. the radioligand is [$^{125}$I]iodocyanopindolol,
4. (−)-isoproterenol (50 μM) is used to define specific binding, and
5. the filters are washed at 4° C.

The $\beta_3$-effect of the compounds is determined by their ability to stimulate adipocyte lipolysis. Rat epididymal fat pads are excised and placed in 0.9% saline. Four grams of tissue is transferred to a flask with 20 ml of aerated Krebs-Henseleit bicarbonate (KHB) buffer containing 3% fatty acid-free bovine serum albumin to which 75 mg of crude bacterial collagenase (Worthington) has been added. The tissue is incubated for about 45 minutes at 37° C. with gentle shaking. The cells are then washed three times with two volumes of KHB buffer, filtered through two layers of gauze, and brought to a final volume of 80 ml with KHB buffer. One ml aliquots of the cell suspension is added to plastic test tubes containing the appropriate additions of vehicle or compound. The cells are gassed for 1 minute with 95%$O_2$-5%$CO_2$, capped, and incubated at 37° C. with continuous shaking for a total of 30 minutes. The reaction is stopped by adding 0.1 ml of 30% perchloric acid and 0.1 ml of chloroform. After centrifugation, 0.5 ml of supernatant is transferred to another test tube and neutralized with 0.04 ml of 3M $K_2CO_3$-0.5M triethanolamine. The amount of glycerol generated from the hydrolysis of endogenous triglycerides is determined in a coupled-enzyme spectrophotometric assay. One-tenth milliliter of the neutralized extract is added to a test tube that contains 0.91 ml of assay mixture comprised of the following: 0.84M glycine, 0.42M hydrazine sulfate, 4.2 mM EDTA, 0.9 mM β-NAD, 9.9 mM $MgCl_2$, 1 mM ATP, 17 U of glycerophosphate dehydrogenase, and 4.3 U of glycerokinase. The test tubes are incubated for 40 minutes at 37° C. with constant shaking. The amount of NADH generated, which is proportional to the amount of glycerol, is determined by the increase in absorbance at 340 nm. This value is corrected for the amount of NADH generated in the absence of glycerol by incubating another aliquot of the neutralized extract with the same assay mixture but without glycerokinase. The molar $ED_{50}$ value is the molar concentration of compound that gives 50% of the maximum rate of lipolysis of that compound.

TABLE 1

| | beta$_3$ Selectivity Comparison | | |
|---|---|---|---|
| Compound | Lipolysis (beta$_3$)(EC$_{50}$ nM) | Heart Binding (IC$_{50}$ nM) | Lung Binding (IC$_{50}$) |
| Example 5 | 100 | >1,000 | >1,000 |
| Example 4 | 14.6 | >1,000 | >1,000 |
| Example 3 | 2,586 | >1,000 | >1,000 |
| Example 7 | 4,000 | >1,000 | >1,000 |

When tested by methods described in U.S. Pat. No. 5,061,727 (Bloom, et al.) for reduction of serum glucose levels, and weight loss in mice, the compounds of this invention did not show significant activity at the dose levels tested. However, the lipolysis data of Table 1 suggest that weight loss and glucose reduction should be observed at higher levels.

These compounds may be active in other therapeutic areas in which selective β$_3$-adrenergic activity is beneficial.

In addition to the abilities of the compounds described hereinabove, some of the compounds are useful as intermediates in the preparation of other compounds described in the present invention.

The compounds of the present invention may generally be prepared according to Schemes 1-3.

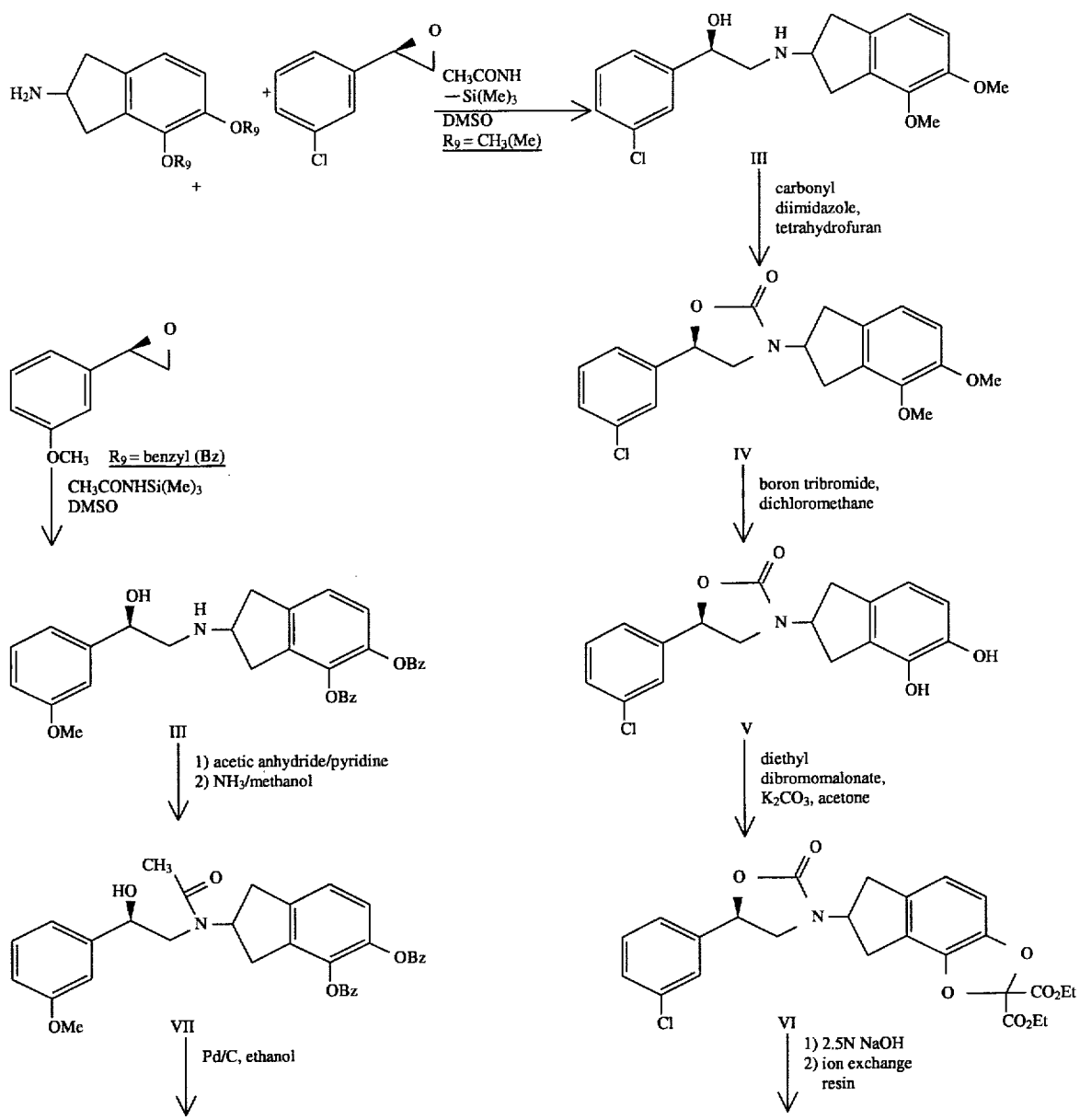

Scheme 1

-continued
Scheme 1

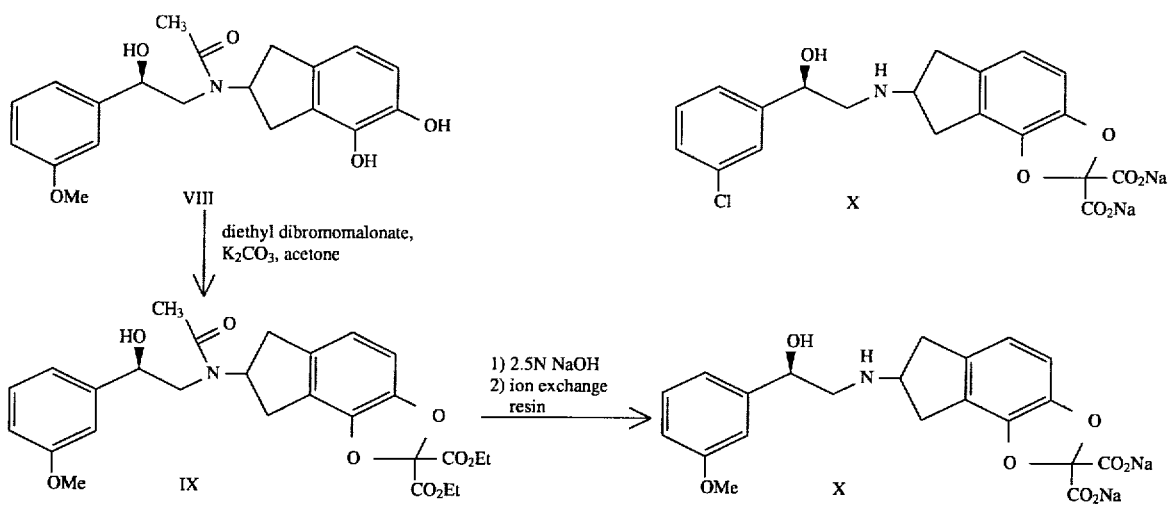

According to Scheme 1, a compound of the formula:

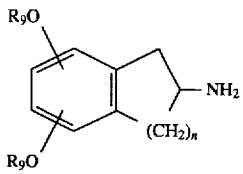

wherein n is an integer from 1–3; the $R_9O$— groups are ortho to each other, $R_9$ is methyl, benzyl or —$SiR_{10}$ wherein $R_{10}$ is trimethyl or triethyl is reacted with a compound of the formula:

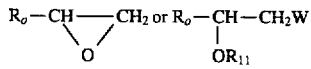

wherein $R_o$ is as defined hereinabove and $R_{11}$ is hydrogen or —$Si(CH_3)_3$; W is bromine, chlorine, iodine, $CH_3SO_2$— or p-toluenesulfonyl in a solvent such as ethanol, isopropyl alcohol or dimethyl sulfoxide in the presence of $CH_3C(=O)$—$NHSi(CH_3)_3$ when the epoxide is used; or a compound of the formula:

II wherein $R_9$ and n are as defined hereinabove is reacted with an amino alcohol of the formula:

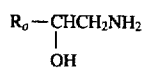

wherein $R_o$ is as defined hereinabove, in the presence of sodium cyanoborohydride in a solvent such as water, methyl alcohol, ethyl alcohol or tetrahydrofuran, at temperatures from 0°–35° C., for 0.5–3 hours, to give a compound of the formula:

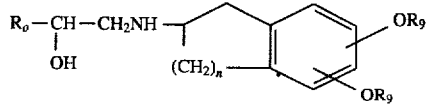

III wherein n, $R_o$ and $R_9$ are as defined hereinabove.

A compound of formula III, wherein n and $R_o$ are as defined hereinabove and $R_9$ is $CH_3$, is reacted with a reagent such as V—C(=Z)—V, wherein V is chlorine, —$OCH_3$, imidazolyl and Z is oxygen or sulfur, in an aprotic solvent such as tetrahydrofuran, at temperatures from 0°–40° C., from 0.5–36 hours, to give a compound of the formula:

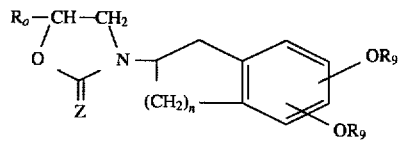

IV wherein n, $R_o$, $R_9$ and Z are as defined hereinabove; followed by a reagent such as $BBr_3$ in an aprotic inert solvent such as methylene chloride to give a compound of the formula:

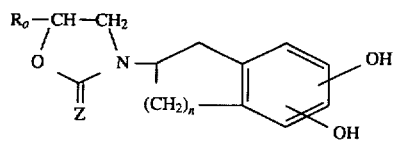

V wherein n, $R_o$ and Z are as defined hereinabove and the hydroxyl groups are in the ortho orientation; and then a compound of formula V is reacted with a compound such as $R_{12}O_2C$—C(=U)—$CO_2R_{12}$ wherein $R_{12}$ is a ($C_1$-$C_4$)alkyl and U is $Br_2$ or an oxygen atom in the presence of acetone and potassium carbonate when U is $Br_2$, or p-toluenesulfonic acid and toluene when U is oxygen to give a compound of the formula:

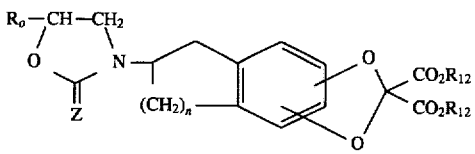

VI wherein n, $R_o$, Z and $R_{12}$ are as defined hereinabove.

A compound of formula III, wherein $R_o$ is as defined hereinabove and $R_9$ is a benzyl group, is reacted with an acylating agent, $R_{13}C(=O)$—T, wherein $R_{13}$ is $(C_1-C_4)$alkyl, phenyl or methoxy such as acetyl chloride, benzoyl chloride, acetic anhydride, methyl chloroformate and the like and T is chlorine, bromine or acetoxy in the presence of a base such as pyridine, sodium acetate or sodium hydroxide followed by isolation of the crude product, and then by digestion with methanolic ammonia at temperatures from 0°–20° C. to give a compound of the formula:

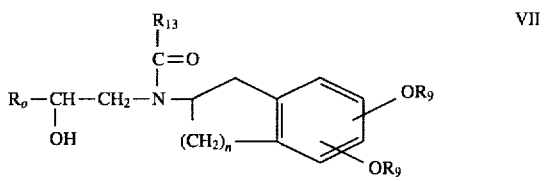
VII wherein n, $R_o$, $R_9$ and $R_{13}$ are as defined hereinabove followed by hydrogenation of a compound such as VII in the presence of a catalyst such as platinum oxide or palladium on carbon, in a solvent such as methyl alcohol, ethyl alcohol, tetrahydrofuran and the like to give a compound of the formula:

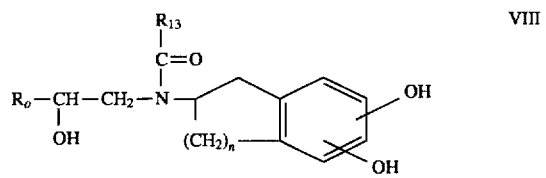
VIII wherein n, $R_o$ and $R_{13}$ are as defined hereinabove, and the hydroxyl groups are in the ortho relationship. A compound of formula VIII is reacted, in a manner as described above for a compound of formula V, with a compound such as $R_{12}O_2C(=U)$—$CO_2R_{12}$, wherein U and $R_{12}$ are as defined hereinabove to give a benzodioxole of the formula:

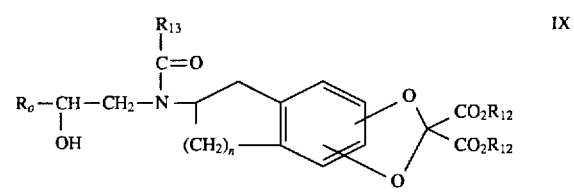
IX wherein n, $R_o$, $R_{12}$ and $R_{13}$ are as defined hereinabove.

A compound of formula VI or IX as defined hereinabove is heated in the presence of a metal base, $M^+OH^-$, wherein $M^+$ is sodium, lithium or potassium, such as NaOH, KOH, LiOH and the like in a solvent such as water, methyl alcohol, ethyl alcohol and the like to give a benzodioxole dicarboxylic acid salt of the formula:

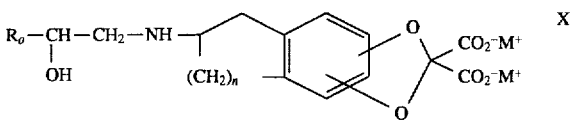
X wherein n, $R_o$ and $M^+$ are as defined hereinabove.

SCHEME 2

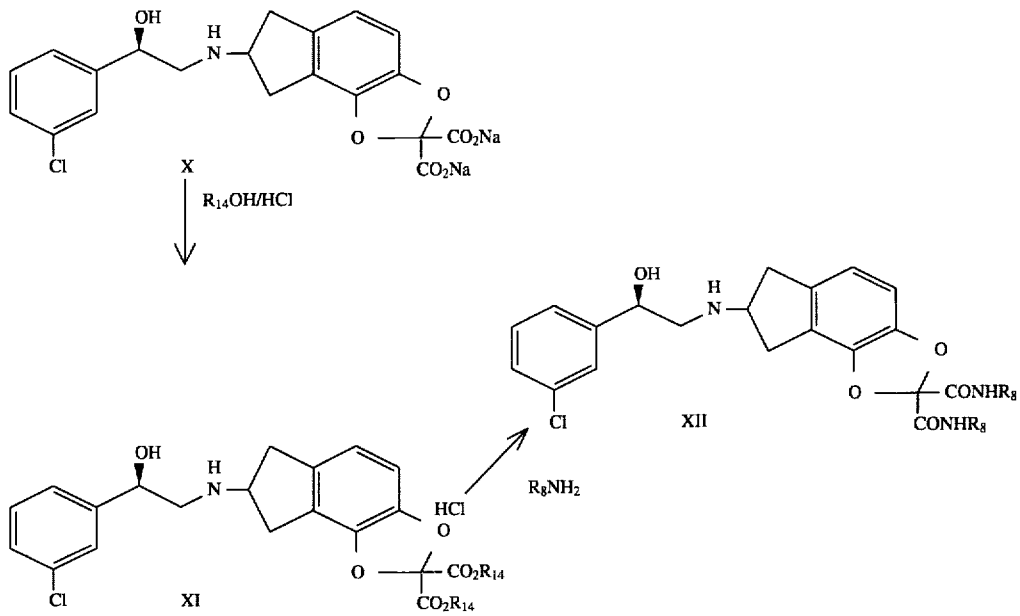

According to Scheme 2, a compound of formula X, as defined hereinabove, can be reacted with an alcohol, $R_{14}OH$, wherein $R_{14}$ is $(C_1-C_{10})$alkyl or alkoxy$(C_1-C_4)$alkyl such as methyl alcohol, ethyl alcohol, isopropyl alcohol or methoxyethanol in the presence of an acid such as HCl, $H_2SO_4$, methanesulfonic acid or p-toluenesulfonic acid to give a compound of the formula:

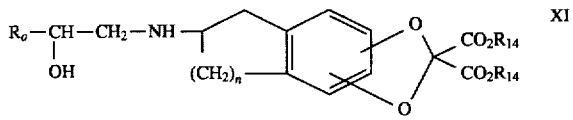
XI wherein n $R_o$ and $R_{14}$ are as defined hereinabove.

A compound of formula XI, as defined hereinabove, can be reacted with a compound of the formula $R_8NH_2$, wherein $R_8$ is a straight or branched $(C_1-C_{10})$-alkyl, alkoxy$(C_1-C_4)$alkyl such as $CH_3OCH_2CH_2$—, substituted phenyl [substitution selected from chlorine, bromine, iodine, fluorine, trifluoromethyl, (C$_1$–C$_4$)alkoxyl or (C$_1$–C$_4$)alkyl], substituted phenyl(C$_1$–C$_4$)alkyl [substitution selected from chlorine, bromine, iodine, fluorine, trifluoromethyl, (C$_1$–C$_4$)alkoxyl or (C$_1$–C$_4$)-alkyl], or heterocycle substituted (C$_1$–C$_4$)alkyl such as

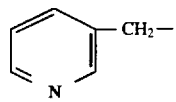

to give a compound of the formula:

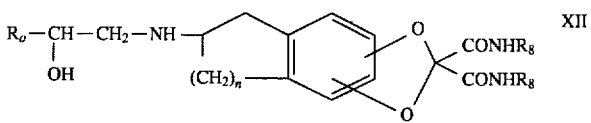

wherein n and R$_o$, and R$_8$ are as defined hereinabove.

Scheme 3

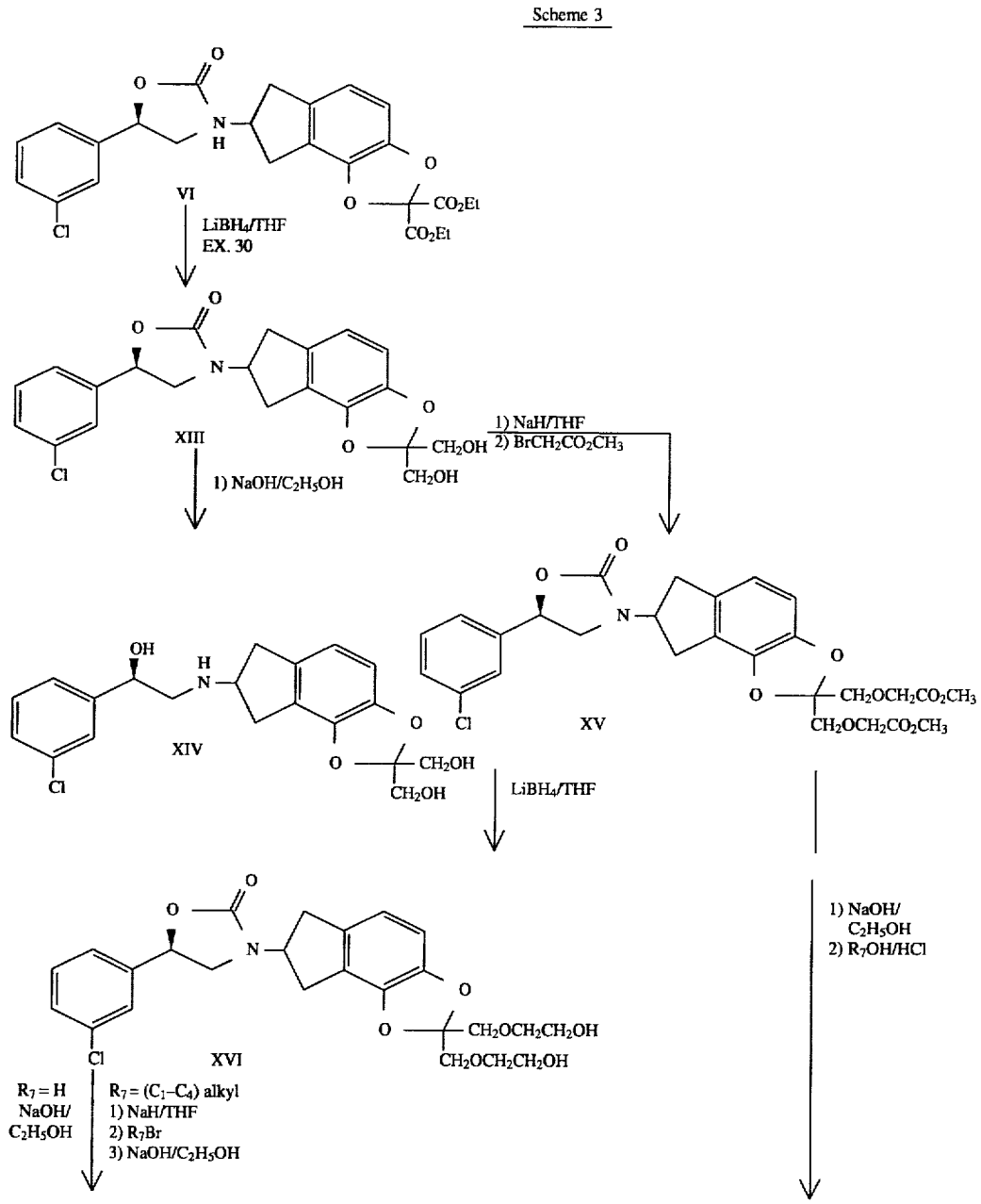

-continued
Scheme 3

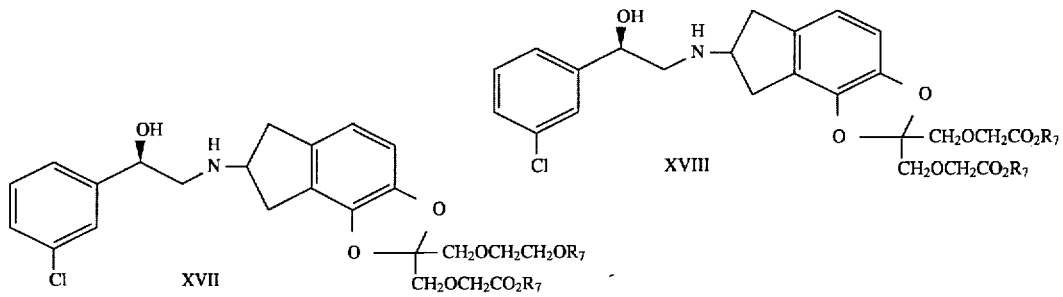

According to Scheme 3, a compound of formula VI can be reduced with a boron hydride such as lithium borohydride in a solvent such as tetrahydrofuran at 0°–25° C. for 30 minutes to 6 hours to give a compound of formula XIII, which is then hydrolyzed with an alkali metal hydroxide such as sodium hydroxide in a solvent such as ethyl alcohol, water or a mixture thereof to give a compound of formula XIV.

A compound of formula XIII can be reacted with a strong base such as sodium hydride in a solvent such as tetrahydrofuran at 0°–25° C. for 30 minutes to one hour followed by addition of an alpha-haloester such as methyl bromoacetate to give a compound of formula XV, which can be reduced with a boron hydride such as lithium borohydride as described above to give a compound of formula XVI. Compound XVI can be reacted with a strong base such as sodium hydride in a solvent such as tetrahydrofuran at 0°–25° C. for 30 minutes to 6 hours followed by the addition of an alkylating agent such as $R_7L$, wherein $R_7$ is as defined hereinabove and L is a leaving group such as bromo, iodo, or p-toluenesulfonyloxy; and followed by hydrolysis with an alkali metal hydroxide such as sodium hydroxide in a solvent such as ethyl alcohol, water or a mixture thereof at 80°–100° C. for 2–24 hours to give a compound of formula XVII.

A compound of formula XV can be hydrolyzed with an alkali metal hydroxide as described previously followed by esterification with an alcohol of the formula $R_7OH$, wherein $R_7$ is as defined hereinabove; in the presence of a mineral acid such as hydrocloric acid or sulfuric acid to give a compound of formula XVIII.

The above mentioned patents and publications are incorporated herein by reference.

When the compounds are employed as anti-diabetic or antiobesity agents, they can be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing for example, from about 20 to 50% ethanol and the like, or parenterally in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

An effective amount of compound from 2.0 mg/kg of body weight to 100.0 mg/kg of body weight should be administered one to five times per day via any typical route of administration including but not limited to oral, parenteral (including subcutaneous, intravenous, intramuscular, intrasternal injection or infusion techniques), topical or rectal, in dosage unit formulations containing conventional non-toxic pharmaceutically acceptable carriers, adjuvants and vehicles. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in glycerol, liquid, polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserve against the contaminating action of microorganisms such as bacterial and fungi. The carrier can be a solvent or dispersion medium containing, for example, water, ethanol, polyol (e.g., glycerol, propylene glycol and liquid polyethylene glycol), suitable mixtures thereof, and vegetable oil.

Many variations of the present invention will suggest themselves to those who are skilled in the art in light of the above mention detailed description. All such obvious modifications are within the full intended scope of the appended claims.

The invention will be more fully described in conjunction with the following specific examples which are not to be construed as limiting the scope of the invention.

EXAMPLE 1

[R-(R*,R* or R*,S*)]-7-[5-(3-Chlorophenyl)-2-oxo-3-oxazolidinyl]-7,8-dihydro-6H-indeno[4,5-d]-1,3-dioxole-2,2-dicarboxylic acid diethyl ester Step A A mixture of 13.7 g of racemic 2-amino-4,5-dimethoxyindane, prepared by the procedure of Cannon, J. G. et al., J. Med. Chem., 25, 1442(1982), 70 ml of dimethyl sulfoxide and 10.24 g of N-trimethylsilylacetamide is stirred under argon at room temperature for 1 hour. To this mixture 11.51 g of (R)-m-chlorostyrene oxide in 10 ml of dimethyl sulfoxide is added. The reaction is stirred under argon at 65°–70° C. for 48 hours. After cooling to room temperature, the reaction mixture is added to 200 g of ice containing 15 ml of concentrated hydrochloric acid and stirred for 15 minutes. Diethyl ether is added and the mixture is stirred until all the solids are dissolved. The layers are separated and the aqueous layer is extracted with diethyl ether, made basic with 10N sodium hydroxide, filtered and re-extracted with diethyl ether. The organic layers are combined, dried over sodium sulfate, filtered and concentrated in vacuo to give 18.6 g of a diastereomeric mixture of 1-(3-chlorophenyl)-2-(4,5-di-methoxyindan-2-yl)aminoethanol as a light yellow oil.

Step B

A mixture of 18.58 g of the above amino-alcohol, 100 ml of anhydrous tetrahydrofuran, 48 ml of triethylamine and 17.35 g of carbonyldiimidazole, under argon, is stirred at room temperature for 20 hours. The reaction mixture is poured into 500 ml of water and extracted with diethyl ether. The organic layers are combined, washed with 2N hydrochloric acid, saturated sodium chloride, dried over magnesium sulfate, filtered and evaporated in vacUo to give 18.7 g of a light brown oil. The residue is purified by chromatography [silica gel: chloroform/hexane/ethyl acetate (3:6:1)] to give 7.85 g of the R,S oxazolidinone isomer-A (less polar component) as a yellow oil and 8.01 g of the R,R oxazolidinone isomer-B (more polar component) as a white solid, mp 106°–107° C.

Step C

To a 0°–4° C. solution, under argon, of 9.34 g of the R,S oxazolidinone isomer-A in 75 ml of methylene chloride is added, dropwise over 40 minutes, 18.8 g of boron tribromide in 15 ml of methylene chloride. The reaction is stirred at this temperature for 20 minutes, and then allowed to warm to room temperature. The reaction is stirred an additional hour at room temperature, recooled to 5° C. and quenched with 100 ml of water. The mixture is allowed to warm to room temperature and stirred an additional hour. The organic layer is separated, washed with saturated sodium chloride, dried over sodium sulfate, filtered and concentrated in vacuo. The residue is dissolved in 150 ml of acetone and treated, under argon, with 17.4 g of powdered potassium carbonate and 8.5 g of diethyl dibromomalonate. The resulting mixture is stirred, under argon, for 18 hours. The reaction is filtered and the insoluble inorganic solids are washed with acetone. The filtrates are combined and concentrated in vacuo. The residue is purified by chromatography (silica gel: 20:1 toluene-:acetone) to give 4.40 g of the desired product as a gum.

$^1$H NMR(CDCl$_3$): δ1.29(t,3H,J=7.1 Hz); 1.33(t,3H,J=7.1 Hz); 2.87–2.98(m,2H); 3.17–3.32(m,3H); 3.68(t,1H,J=8.8 Hz); 4.90(m,1H); 5.41(dd,1H,J=8.6, 7.3 Hz); 4.32(q,2H,J=7.1 Hz); 4.36(q, 2H,J=7.1 Hz); 6.79(s,2H,Ar); 7.17(m,1H, Ar); 7.32(m,3H,Ar).

EXAMPLE 2

[R-(R*,R* or R*,S*)]7-[5-(3-Chlorophenyl)-2-oxo-3-oxazolidinyl]-7,8-dihydro-6H-indeno[4,5-d]-1,3-dioxole-2,2-dicarboxylic acid diethyl ester The title compound is prepared by the procedure of Example 1 using 9.34 g of product from Example 1, Step B, isomer-B, to give 4.99 g of the desired product as a light yellow gum.

$^1$H NMR(CDCl$_3$): δ1.345(t,3H,J=7.1 Hz); 1.351(t,3H,-J= 7.1 Hz); 2.83(dd,1H,J=16.3, 4.8 Hz); 3.00(dd,1H,-J=16.8, 4.7 Hz); 3.12–3.20(m,2H) 3.31(dd,1H,J=16.8, 7.7 Hz); 3.68(t,1H,J=8.8 Hz); 4.37(q,2H,J=7.1 Hz); 4.38(q,2H,J=7.1 Hz); 4.91(m,1H); 5.43(m,1H); 6.74(d,1H,Ar,J=8.0 Hz); 6.78(d,1H,J=8.0 Hz); 7.19(m,1H, Ar); 7.32 (m,3H,Ar).

EXAMPLE 3

[R-(R*,R* or R*,S*)]7-[[2-(3-Chlorophenyl)-2-hydroxyethyl]amino]-7,8-dihydro-6H-indeno[4,5-d]-1,3-dioxole-2,2-dicarboxylic acid disodium salt To 1.60 g of product from Example 1, Step C, under argon, is added 22 ml of 2.5N sodium hydroxide. The reaction mixture is heated to its reflux temperature and maintained at this temperature for 20 hours. The gum that is originally present dissolves and the solution turns a dark brown. The reaction mixture is evaporated in vacuo and the residue treated with ethyl alcohol. The solids are isolated by filtration, rinsed with ethyl alcohol and diethyl ether and air dried briefly. The resulting solid is dissolved in water and loaded onto a column of XAD-4 resin (previously washed with 1 liter of 50:50 methyl alcohol:water, followed by 500 ml of water). The column is eluted with 1 liter of water followed by 1 liter of methyl alcohol. The methyl alcohol fractions containing the Rf 0.60 component (7:1 water:methyl alcohol; reverse phase tlc plates) are combined, evaporated in vacuo and the residue is triturated with ethyl alcohol. The solids are collected, rinsed with ethyl alcohol and air dried to give 0.86 g of the desired product as a light brown solid. $^1$H NMR(D$_2$O): δ2.79(m,2H); 3.01(m,2H); 3.21(m,2H); 3.79(m,1H); methine next to OH approx. 4.86; 6.77(s,2H,Ar); 7.3–7.5(m,4H,Ar).

EXAMPLE 4

[R-(R*,R* or R*,S*)]-7-[[2-(3-Chlorophenyl)-2-hydroxyethyl]amino]-7,8-dihydro-6H-indeno[4,5-d]-1,3-dioxole-2,2-dicarboxylic acid disodium salt The title compound is prepared by the procedure of Example 3 using 1.96 g of product from Example 2 and 27 ml of 2.5N sodium hydroxide. The residue is purified by chromatography as above to give 0.89 g of the desired component as an off white solid, Rf=0.61.

$^1$H NMR(D$_2$O): δ2.79(m,2H); 3.01(m,2H); 3.11–3.30(m, 2H); 3.77(m, 1H); methine next to OH approx. 4.86; 6.77(s, 2H,Ar); 7.32–7.48(m,4H,Ar).

EXAMPLE 5

(R)-7-[[2-(3-Chlorophenyl)-2-hydroxyethyl]amino]7,8-dihydro-6H-indeno[5,6-d]-1,3-dioxole-2,2-dicarboxylic acid disodium salt Following the procedure of Example 1 using 2-amino-5,6-dimethoxyindane, (R)-6-[5-(3-chlorophenyl)-2-oxo-3-oxazolidinyl]-7,8-dihydro-6H-indeno[5,6-d]-1,3-dioxole- 2,2-dicarboxylic acid diethyl ester is obtained.

The title compound is prepared by the procedure of Example 3 using 1.90 g of the above oxazolidinone diester and 26 ml of 2.5N sodium hydroxide. The product is purified by chromatography as in Example 3 giving 1.04 g of a white solid, Rf=0.58.

$^1$H NMR(D$_2$O): δ2.72(m,2H); 2.99(m,2H); 3.13(m,2H); 3.72(m,1H); methine next to OH approx. 4.86; 6.80(s,2H, Ar); 7.32–7.47 (m,4H,Ar).

EXAMPLE 6

(R*,R*) and (R*,S*)-6-[5-(3-Chlorophenyl)-2-oxo-3-oxazolidinyl]-5,6,7,8-tetrahydronaphtho[2,3-d]-1,3-dioxole-2,2-dicarboxylic acid diethyl ester A mixture of 0.83 g of 2-amino-1-(m-chlorophenyl)ethanol, 1.0 g of 6,7-dimethoxy-2-tetralone and 0.85 g of sodium cyanoborohydride in 25 ml of methyl alcohol is stirred at room temperature for 18 hours. The reaction mixture is poured into water and a product residue is isolated. This residue is purified by flash chromatography to give 0.80 g of 3-chloro-α-[[(1,2,3,4-tetrahydro-6,7-dimethoxy)naphthalen-2-yl)amino]methyl]benzenemethanol, which is in turn converted to 5-(3-chlorophenyl-3-(1,2,3,4-tetrahydro-6,7-dimethoxy)naphthalen-2-yl)-2-oxazolidinone. Subsequent reaction with boron tribromide in methylene chloride as in Example 1, Step A, gives 5-(3-chlorophenyl)-3-(1,2,3,4-tetrahydro-6,7-dihydroxynaphthalen-2-yl)-2-oxazolidinone as a solid, mp 195° C. (dec.).

A mixture of 0.90 g of the above catechol derivative, 0.836 g of diethyl dibromomalonate and 1.8 g of powdered anhydrous potassium carbonate in 15 ml of acetone is stirred at room temperature for 18 hours. The reaction mixture is filtered and concentrated in vacuo to give 0.708 g of a mixture of diastereomers as a colorless oil.

Calculated for C$_{26}$H$_{26}$NClO$_8$: Theory: C, 60.53; H, 5.08; N, 2.71; Cl, 6.87 Found: C, 61.13; H, 5.18; N, 2.49; Cl, 6.50.

EXAMPLE 7

(R*,R*), and (R*,S*)-6-[[2-(3-Chlorophenyl)-2-hydroxyethyl]amino]-5,6,7,8-tetrahydronaphtho[2,3-d]-1,3-dioxole-2,3-dicarboxylic acid disodium salt A mixture, under argon, of 0.625 g of product from Example 6 and 5 ml of 2.5N sodium hydroxide is heated at reflux temperature for 18 hours. The reaction mixture is cooled and then concentrated hydrochloric acid is added until pH 10 is reached. The product residue is purified by chromatography (C$_{18}$-octadecyl silica gel) to give 0.35 g of a mixture of diastereomers as a solid.

Calculated for C$_{21}$H$_{18}$NClO$_7$Na$_2$ 0.31H$_2$O: Theory: C, 52.18; H, 3.88; N, 2.90; Cl, 7.33; Na, 9.51; H$_2$O, 1.16 Found: C, 49.99; H, 3.73; N, 2.65; Cl, 6.86; Na, 8.34; H$_2$O, 1.16.

EXAMPLE 8

(R*,R*), and (R*,S*)-6-[[2-(3-Chlorophenyl)-2-hydroxyethyl]amino]-5,6,7,8-tetrahydronaphtho[1,2,-d]-1,3-dioxole-2,2-dicarboxylic acid disodium salt Following the procedure of Example 1 using 2-amino-5,6-dimethoxytetralin, (R*,R*), and (R*,S*)-6-[5-(3-chlorophenyl)-2-oxo-3-oxazolidinyl]-4,5,6,7tetrahydronaphtho [1,2-d]-1,3-dioxole-2,2-dicarboxylic acid diethyl esters are obtained.

The title compounds are prepared by the procedure of Example 3 using 1.90 g of the oxazolidinone diesters from above and 26 ml of 2.5N sodium hydroxide for each. Purification by chromatography (silica gel) gives the (R*, R*), and (R*,S*) enantiomeric pairs.

EXAMPLE 9–12 (TABLE 1)

Substantially following the methods described in detail hereinabove in Examples 1 and 3, using the appropriately substituted phenyloxirane, the compounds of this invention listed below in Examples 9–12 are prepared.

TABLE 1

| Example | Phenyl-oxirane | Substituted phenyl-2-hydroxyethyl]amino-7,8-dihydro-6H-indeno [4,5-d]-1,3-dioxole-2,2-dicarboxylic acid disodium salt |
|---|---|---|
| 9 | 3-Fluoro | 7-[[2-(3-Fluorophenyl)-2-hydroxyethyl]amino-7,8-dihydro-6H-indeno(4,5-d]-1,3-dioxole-2,2-dicarboxylic acid disodium salt |
| 10 | 3-Bromo | 7-[[2-(3-Bromophenyl)-2-hydroxyethyl]amino-7,8-dihydro-6H-indeno[4,5-d]-1,3-dioxole-2,2-dicarboxylic acid disodium salt |
| 11 | 3-Iodo | 7-[[2-(3-Iodophenyl)-2-hydroxyethyl]amino-7,8-dihydro-6H-indeno[4,5-d]-1,3-dioxole-2,2-dicarboxylic acid disodium salt |
| 12 | 4-Chloro | 7-[[2-(4-Chlorophenyl)-2-hydroxyethyl]amino-7,8-dihydro-6H-indeno[4,5-d]-1,3-dioxole-2,2-dicarboxylic acid disodium salt |

EXAMPLE 13

(R*,R*), and (R*,S*)-N-Acetyl-7-[5-(3-methoxyphenyl)2-hydroxyethyl]amino-7,8-dihydro-6H-indeno[4,5-d-1,3-dioxol-2,2-dicarboxylic acid diethyl ester Acetic anhydride is added to a mixture of 2-amino-4,5-dihydroxyindane [Cannon, J. G., et al., J. Med. Chem. 27, 922(1984)] in water containing sodium acetate. The mixture is chilled and stirred in ice for 4 hours followed by filtration to give N-acetyl-2-amino-4,5-dihydroxyindane. Benzylbromide, powdered potassium carbonate and acetone is added to the isolated N-acetyl-2-amino-4,5-dihydroxyindane and the mixture is stirred for 18 hours. The reaction mixture is poured into water, extracted and evaporated in vacuo to give N-acetyl-2-amino-4,5-dibenzyloxyindane. Hydrolysis with ethanolic sodium hydroxide gives 2-amino-4,5-dibenzyloxyindane.

The title compound is prepared by the procedure of Example 1, Step A, using 24.5 g of racemic 2-amino-4,5-dibenzyloxyindane, 70 ml of dimethyl sulfoxide and 10.24 g of N-trimethylsilylacetamide to give a diastereomeric mixture of 1-(3-methoxyphenyl)2-(4,5-dibenzyloxyindan-2-yl)aminoethanol.

The above amino-alcohol is combined with excess acetic anhydride in pyridine and allowed to stand at room temperature for 18 hours. The reaction mixture is poured into water, the diacetyl product is dissolved in methyl alcohol and the solution is saturated with ammonia gas. The reaction is maintained at 0° C. for 24 hours. Concentration in vacuo gives N-acetyl-1-(3-methoxyphenyl)-2-(4,5-dibenzyloxyindan-2-yl)aminoethanol, which is subjected to hydrogenolysis in ethyl alcohol in the presence of 5% palladium on carbon at atmospheric pressure to give N-acetyl-1-(3-methoxyphenyl)-2-(4,5-dihydroxyindan-2-yl)aminoethanol. Treatment of the above product with diethyl dibromomalonate and powdered potassium carbonate in dry acetone for 72 hours gives the desired product. Purification by chromatography (silica gel) gives the (R*,R*) and (R*,S*) enantiomeric pairs.

EXAMPLE 14

(R*,R*)-7-[5-(3-Methoxyphenyl)-2-hydroxyethyl]amino]-7,8-dihydro-6H-indeno[4,5-d]-1,3-dioxole-2,2-dicarboxylic acid disodium salt The title compound is prepared by the procedure of Example 3 using the (R*,R*)-product from Example 12, 2.5N sodium hydroxide and purifying the product by chromatography.

EXAMPLE 15

(R*,S*)-7-[5-(3-Methoxyphenyl)-2-hydroxyethyl]amino]7,8-dihydro-6H-indeno[4,5-d]-1,3-dioxole-2,2-dicarboxylic acid disodium salt The title compound is prepared by the procedure of Example 3 using the (R*,S*)-product from Example 12, 2.5N sodium hydroxide and purifying the product by chromatography.

EXAMPLE 16–19 (TABLE 2)

Substantially following the methods described in detail hereinabove in Example 13 and 3, using the appropriately substituted phenyloxirane, the compounds of this invention listed below in Examples 16–19 are prepared.

TABLE 2

Substituted phenyl-2-hydroxyethyl]amino-7,8-dihydro-6H-indeno [4,5-d]-1,3-dioxole-2,2-dicarboxylic acid disodium salt

| | | |
|---|---|---|
| 16 | 2-Naphthyl | 7-[[(2-(2-Naphthyl)-2-hydroxyethyl]amino-7,8-dihydro-6H-indeno[4,5-d]-1,3-dioxole-2,2-dicarboxylic acid disodium salt |
| 17 | 3-Methylphenyl | 7-[[2-(3-Methyl)-2-hydroxyethyl]amino-7,8-dihydro-6H-indeno[4,5-d]-1,3-dioxole-2,2-dicarboxylic acid disodium salt |
| 18 | 3,4-Dimethoxyphenyl | 7-[[2-(3,4-Dimethoxyphenyl)-2-hydroxyethyl]amino-7,8-dihydro-6H-indeno[4,5-d]-1,3-dioxole-2,2-dicarboxylic acid disodium salt |
| 19 | 1-Naphthyl | 7-[[2-(1-Naphthyl)-2-hydroxyethyl]amino-7,8-dihydro-6H-indeno[4,5-d]-1,3-dioxole-2,2-dicarboxylic acid disodium salt |

EXAMPLE 20

(R*,R*) and (R*,S*)-6-[[2-(3-Chlorophenyl)-2-hydroxyethyl]amino-5,6,7,8-tetrahyronaphtho[2,3-d]-1,3-dioxole-2,2-dicarboxylic acid dimethyl ester hydrochloride A suspension of product from Example 7 in absolute methyl alcohol is saturated with gaseous hydrogen chloride and stirred at room temperature for 20 hours. The reaction mixture is filtered and the filtrate evaporated in vacuo to give the desired product.

EXAMPLE 2

(R*,R*) and (R*,S*)-6-[[2-(3-Chlorophenyl)-2-hydroxyethyl]amino-5,6,7,8-tetrahydronaphtho[2,3-d]-1,3-dioxole-2,2-dicarboxylic acid diethyl ester hydrochloride A solution of product from Example 20 in ethyl alcohol is saturated with gaseous hydrogen chloride and stirred at room temperature for 20 hours. The reaction mixture is evaporated in vacuo to give the desired product.

EXAMPLE 22–25 (TABLE 3)

Substantially following the method described in detail hereinabove in Example 21, using the appropriate alcohol, the compounds of this invention listed below in Examples 22–25 are prepared.

TABLE 3

| Example | Alcohol | Product |
|---|---|---|
| 22 | 1-Propanol | R*,R*) and (R*,S*)-6-[[2-(3-Chlorophenyl)-2-hydroxyethyl]amino]-5,6,7,8-tetrahydro-naphtho-[2,3-d]-1,3-dioxole-2,2-dicarboxylic acid dipropylester hydrochloride |
| 23 | 2-Propanol | (R*,R*) and (R*,S*)-6-[[2-(3-Chlorophenyl)-2-hydroxy-ethyl]amino]-5,6,7,8-tetrahydro-naphtho-[2,3-d]-1,3-dioxole-2,2-dicarboxylic acid diisopropylester hydrochloride |
| 24 | 1-Butanol | (R*,R*) and (R*,S*)-6-[[2-(3-Chlorophenyl)-2-hydroxy-ethyl]amino]-5,6,7,8-tetrahydro-naphtho-[2,3-d]-1,3-dioxole-2,2-dicarboxylic acid dibutyl ester hydrochloride |
| 25 | Methoxyethanol | (R*,R*) and (R*,S*)-6-[[2-(3-Chlorophenyl)-2-hydroxy-ethyl]amino]-5,6,7,8-tetrahydro-naphtho-[2,3-d]-1,3-dioxole-2,2-dicarboxylic acid dimethoxyethyl ester hydrochloride |

EXAMPLE 26

(R*,R*) and (R*,S*)-6-[[2-(3-Chlorophenyl)-2-hydroxyethyl]amino-5,6,7,8-tetrahydronaphtho[2,3-d]-1,3-dioxole-2,2-dicarboxylic acid di(methoxyethyl)amide hydrochloride A solution of product from Example 20 in ethyl alcohol is stirred at room temperature for 20 hours with an excess of methoxyethylamine. The reaction mixture is evaporated in vacuo and combined with a sodium carbonate solution and diethyl ether. The layers are separated and the diethyl ether layer is dried over sodium sulfate and filtered. Gaseous hydrogen chloride is bubbled into the filtered diethyl ether solution and the desired product is collected.

EXAMPLE 27

(R*,R*) and
(R*,S*)-7-[[2-(3-Trifluoromethylphenyl)-2-hydroxyethyl]amino-7,8-dihydro-6H-indeno[4,5-d-1,3-dioxole-2,2-dicarboxylic acid disodium salt A solution of m-trifluoromethylphenylglyoxal and 2-amino-4,5-dimethyoxyindane in toluene is refluxed for 2 hours, using a Dean-Stark trap to remove the formed water. The solution is concentrated in vacuo and the residue is dissolved in methyl alcohol. The resulting solution is cooled in ice, sodium borohydride is added in portions and the reaction mixture is stirred at room temperature for 2 hours. The reaction mixture is concentrated in vacuo, the residue is partitioned between water and methylene chloride and the layers are separated. The organic layer is dried over sodium sulfate and concentrated in vacuo to give 1-(3-trifluoromethylphenyl)-2-(4,5-dimethoxyindan-2-yl)aminoethanol. Under anhydrous conditions, tetrahydrofuran, triethylamine and carbonyldiimidazole are added to the above compound and the mixture is stirred at room temperature for 20 hours. The reaction mixture is quenched with water and extracted with diethyl ether. The diethyl ether extracts are combined, washed with 2N hydrochloric acid, saturated sodium chloride, dried over magnesium sulfate. The solution is evaporated in vacuo to give a mixture of (R*,R*) and (R*,S*)-5-(3-trifluoromethylphenyl)-3-(2,3-dihydro-4,5-dimethoxy-1H-inden-2-yl)-2-oxazolidinone. This mixture is separated into the individual (R*,R*) and (R*,S*) racemates by chromatographic techniques described in Example 1. Each racemate is treated with boron tribromide and the individual products are reacted with diethyl dibromomalonate, as described in Example 1, to give (R*,R*) and (R*,S*)-7-[[2-(3-trifluoromethylphenyl)-2-hydroxyethyl]amino]-7,8-dihydro-6H-indeno[4,5-d]-1,3-dioxole-2,2-dicarboxylic acid diethyl esters. These products are then hydrolyzed with 2.5N sodium hydroxide, as described in Example 3, to give the desired products.

EXAMPLE 28

(R*,R*) and (R*,S*)-6-[[2-(3-Methoxyphenyl)-2-hydroxyethyl]amino-6,7,8,9-tetrahydro-5H-cycloheptenobenzo[1,2-d]-1,3-dioxole-2,2-dicarboxylic acid diethyl ester Acetic anhydride is added to a mixture of 6-amino-6,7, 8,9-tetrahydro-5H-cycloheptene-1,2-diol [Cannon, J. G., et al., *J. Med. Chem.*, 27, 922(1984)] in water containing sodium acetate. The mixture is chilled and stirred in ice for 4 hours followed by filtration to give N-acetyl-6-amino-6, 7,8,9-tetrahydro5H-benzocycloheptene-1,2-diol. Benzyl bromide, powdered potassium carbonate and acetone is added to the isolated N-acetyl-6-amino-6,7,8,9-tetrahydro-5H-benzocycloheptene-1,2-diol and the mixture is stirred for 18 hours. The reaction mixture is poured into water, extracted and concentrated in vacuo to give N-acetyl-6-amino-1,2-dibenzyloxy-6,7,8,9-tetrahydro-5H-benzocycloheptene. Hydrolysis with ethanolic sodium hydroxide gives 6-amino-1,2-dibenzyloxy-6,7,8,9-tetrahydro-5H-benzocycloheptene.

A mixture of 26 g of racemic 6-amino-1,2-dibenzyloxy-6,7,8,9-tetrahydro-5H-benzocycloheptene, 70 ml of dimethyl sulfoxide and 10.2 g of N-trimethylsilylacetamide is stirred, under argon, at room temperature for 1 hour. To this mixture is added 15 g of m-methoxystyrene oxide in 10 ml of dimethyl sulfoxide and the reaction mixture is heated, under argon, at 65°–70° C., for 48 hours. After cooling to room temperature, the reaction mixture is added to 200 g of ice containing 15 ml of concentrated hydrochloric acid and stirred for an additional 15 minutes. Diethyl ether is added and the mixture is stirred until all solid is dissolved. The layers are separated and the aqueous layer is reextracted (2×) with diethyl ether. The aqueous layer is made basic with 10N sodium hydroxide and reextracted (3×) with diethyl ether. The diethyl ether layers are combined, dried over sodium sulfate and evaporated in vacuo to give a diastereomeric mixture of 1-(3-methoxyphenyl)-2-[1,2-dibenzyloxy-6,7,8, 9-tetrahydro-5H-benzocyclohepten)-6-yl]aminoethanol.

The above amino-alcohol is combined with excess acetic anhydride in pyridine, stirred for 18 hours and then poured into water. The diacetyl product is dissolved in methyl alcohol, saturated with ammonia gas and allowed to stand at 0° C. for 24 hours. The reaction is evaporated in vacuo to give N-acetyl-(3-methoxyphenyl)-2-[(1,2-dibenzyloxy-6,7, 8,9tetrahydro-5H-benzocyclohepten)-6-yl]aminoethanol. Hydrogenation of the above compound in ethyl alcohol with 5% palladium on carbon at atmospheric pressure gives N-acetyl-(3-methoxyphenyl)-2-[(1,2-dihydroxy-6,7,8,9-tetrahydro5H-benzocyclohepten)-6-yl]aminoethanol. Diethyl dibromomalonate and powdered potassium carbonate in dry acetone are added to the above compound and the mixture is stirred at room temperature for 72 hours. The reaction mixture is filtered and evaporated in vacuo to give the desired product as a diastereomeric mixture. The enantiomeric pairs, (R*,R*) and (R*,S*), are isolated after chromatography on silica gel.

EXAMPLE 29

(R*,R*) and (R*,R*)-6-[[2-(3-Methoxyphenyl)-2-hydroxyethyl]amino-6,7,8,9-tetrahydro-5H-cycloheptenobenzo[1,2-d]-1,3-dioxole-2,2-dicarboxylic acid disodium salt (R*,R*) and (R*,S*)-6-[[2-(3-Methoxyphenyl)2-hydroxy-ethyl]amino-6,7,8,9-tetrahydro-5H-cycloheptenobenzo-[1,2-d]-1,3-dioxole-2,2-dicarboxylic acid diethyl esters are each treated with 2.5N sodium hydroxide. Each mixture is heated for 18 hours at reflux, under argon, evaporated in vacuo and the residues treated with ethyl alcohol. The resulting solids are collected, rinsed with ethyl alcohol and diethyl ether and briefly air dried. The solid product is dissolved in water and loaded onto a column of XAD-4 resin, previously washed with 50:50 methyl alcohol:water and then water. The column is eluted with water followed by methyl alcohol. The methyl alcohol fractions are combined and evaporated in vacuo. For each, the residue is triturated with ethyl alcohol, the solid collected, rinsed with ethyl alcohol and air dried to give the desired products.

EXAMPLE 30

(R*,R*)-7-[5-(3-Chlorophenyl)-2-oxo-3-oxazolidinyl]-1,3-(7,8-dihydro-6H-indeno[4,5-d])dioxole-2,2-diyl)bis (methyleneoxy)bis acetic acid dimethyl ester A mixture of 1.63 g of product from Example 2, 2.5 g of lithium borohydride and 25 ml of anhydrous tetrahydrofuran is reacted to give (R*,R*)-7-[5-(3-chlorophenyl)-2-oxo-3-oxazolidinyl]-1,3-(7,8-dihydro6H-indeno[4,5-d])dioxole-2,2-diyl)bishydroxymethylene as a solid.

To a hexane washed portion of 60% sodium hydride is added, under agon, the above glycol in tetrahydrofuran. The solution is stirred for 5 minutes, followed by the addition of methyl bromoacetate over a ten minutes span. The reaction is stirred overnight at room temperature, poured into aqueous ammonium chloride and extracted twice with ethyl acetate. The organic extracts are combined, dried and evaporated to an oil which is purified by chromatography to give the desired product as a solid.

EXAMPLE 3

(R*,R*)-7-[5-(3-Chlorophenyl)-2-oxo-3-oxazolidinyl]-(7,8-dihydro-6H-indeno[4,5-d])-2,2-bis(2-hydroxyethoxymethyl)-1,3-dioxole A mixture of 0.420 g of product from Example 30, 0.75 g of lithium borohydride and 10 ml of anhydrous tetrahydrofuran is reacted for 1.5 hours to give, after purification by chromatography, the desired product.

EXAMPLE 32

(R*,R*)-7-[[2-(3-Chlorophenyl)-2-hydroxyethyl]amino]7,8-dihydro-6H-indeno[4,5-d]-1,3-dioxole-2,2-diylbismethyleneoxy)bis acetic acid dimethyl ester A mixture of 0.37 g of product from Example 30, 9 ml of 5N sodium hydroxide and 19 ml of absolute ethanol is heated at reflux temperature overnight. The reaction mixture is cooled, acidified to pH 5 with concentrated hydrochloric acid, evaporated to dryness in vacuo and the residue is dissolved in 20 ml of methyl alcohol. The solution is saturated with hydrogen chloride gas and stirred for 1.5 hours. The reaction mixture is poured into aqueous sodium bicarbonate and extracted twice with ethyl acetate. The extracts are combined, washed with brine, dried and evaporated. The residue is purified by flash chromatography, eluting with ethyl acetate to give the desired product as a thick oil.

EXAMPLE 33

(R*,R*)-7-[[2-(3-Chlorophenyl)-2-hydroxyethyl]amino]-7,8-dihydro-6H-indeno[4,5-d]-2,2-bis(hydroxyethoxymethyl)-1,3-dioxole A mixture of 0.270 g of product from Example 31, 200 ml of ethyl alcohol, and 5 ml of 5N sodium hydroxide is heated at reflus temperature, under argon, for 8 hours. The reaction mixture is cooled, poured into water containing sodium chloride, and extracted twice with ethyl acetate. The extracts are combined, washed with saturated sodium chloride, dried and evaporated. The residue is purified by flash chromatography, eluting with methylene chloride:methyl alcohol:ammonium hydroxide (250:35:5) to give the desired product as an oil.

EXAMPLE 34

(R*,R*)-7-[[2-(3-Chlorophenyl)-2-hydroxyethyl]amino]-7,8-dihydro-6H-indeno[4,5-d]-2,2-bis(2-methoxyethoxymethyl)-1,3-dioxole A mixture of product from Example 31, sodium hydride, and N,N-dimethylformamide is stirred, under argon, for 1 hour, followed by the addition of methyl iodide. The mixture is stirred at room temperature for hours, poured into water and the precipitated material is extracted into diethyl ether. The extracts are combined, dried and evaporated. The residue is dissolved in a mixture of ethyl alcohol and 5N sodium hydroxide and heated, under argon, at reflux temperature. The reaction mixture is poured into water, extracted with ethyl acetate, dried and evaporated to give the desired product.

We claim:

1. A method of treating hyperglycemia in mammals which comprises administering to a hyperglycemic patient an antihyperglycemic effective amount of a compound of the formula:

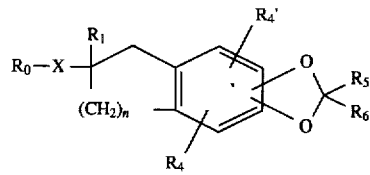

wherein:

$R_o$ is naphthyl, 5,6,7,8-tetrahydronaphth-(1 or 2)-yl, 5,8-dihydronaphth-(1 or 2)-yl; or

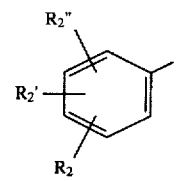

and $R_2$, $R_2'$, $R_2''$ may be the same or different and are hydrogen, $(C_1-C_4)$alkyl, $(C_1-C_4)$alkoxy, hydroxy, halogen (chlorine, bromine, fluorine or iodine), trifluoromethyl, carboxy, hydroxy$(C_1-C_{10})$ alkyl, $(C_1-C_{10})$-alkoxycarbonyl or thio$(C_1-C_4)$alkyl; n is an integer from 1 to 3;

X is the divalent radical:

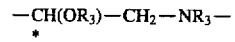

wherein $R_3$ is hydrogen, $(C_1-C_4)$alkyl, $(C_1-C_4)$acyl, $(C_1-C_4)$alkoxycarbonyl or benzoyl; and wherein * denotes an asymmetric carbon;

$R_1$ is hydrogen or $(C_1-C_4)$alkyl; $R_4$ and $R_4'$ may be the same or different and are hydrogen, $(C_1-C_4)$ alkyl, $(C_1-C_4)$alkoxy, hydroxy, halogen (chloride, bromine, fluorine or iodine), trifluoromethyl, carboxy, hydroxy$(C_1-C_{10})$alkyl, $(C_1-C_{10})$alkoxycarbonyl or thio$(C_1-C_4)$alkyl;

$R_5$ and $R_6$ hydrogen, carboxyl, $(C_1-C_{10})$alkoxycarbonyl, hydroxymethyl, —CH$_2$OCH$_2$COOR$_7$ or —CH$_2$OCH$_2$CH$_2$OR$_7$, wherein $R_7$ is hydrogen, or $(C_1-C_4)$alkyl, or CONHR$_8$, $R_8$ is hydrogen, straight or branched $(C_1-C_{10})$alkyl or 2-methoxy-1-ethyl; with the proviso that $R_5$ and $R_6$ may not both be hydrogen; and the pharmacologically acceptable salt or ester thereof; the racemic mixture thereof or the stereoisomeric mixture thereof.

2. A method as defined in claim 1 wherein $R_1$ is hydrogen, n is an integer of 1 or 2, and $R_5$ and $R_6$ are the same and are carboxy, $(C_1-C_{10})$alkoxycarbonyl or alkali metal carboxylate.

3. A method as defined in claim 1 wherein $R_4$ and $R_{4'}$ are hydrogen.

4. A method as defined in claim 1 wherein $R_2$ is $(C_1-C_4)$alkyl, $(C_1-C_4)$alkoxy, hydroxy, halogen, (chlorine, bromine, fluorine or iodine), trifluoromethyl, carboxy, hydroxy$(C_1-C_{10})$alkyl, $(C_1-C_{10})$alkoxycarbonyl, or thio$(C_1-C_4)$alkyl; and $R_{2'}$ and $R_{2''}$ are hydrogen.

5. A method as defined in claim 4 wherein $R_2$ is a chloro substituent.

6. A method according to claim 5, wherein $R_1$, $R_4$ and $R_{4'}$ are hydrogen.

7. A method according to claim 6 wherein $R_5$ and $R_6$ are carboxy.

8. A method according to claim 6 wherein $R_5$ and $R_6$ are $-CO_2CH(CH_3)_2$.

9. A method as defined in claim 8 wherein $R_2$ is a chloro substituent at the 3 position.

10. A method as defined in claim 6 wherein $R_5$ and $R_6$ are $-CO_2^-$ $Na^+$.

11. A method as defined in claim 1 wherein the compound is a racemic compound according which is (R*,S*)-6[[2-(3-chlorophenyl)-2-hydroxyethyl]amino]-5,6,7,8-tetrahydronaphtho[1,2-d]-1,3-dioxole-2,2-dicarboxylic acid disodium salt.

12. A method as defined in claim 1 wherein the compound is an optically active compound which is (R,R)-7-[[2-(3-chlorophenyl)-2-hydroxyethyl]amino]-7,8-dihydro-6H-indeno[4,5-d]-1,3-dioxole-2,2-dicarboxylic acid, disodium salt.

13. A method as defined in claim 1 wherein the compound is an optically active compound which is (R,R)-7-[[2-(3-chlorophenyl)-2-hydroxyethyl]amino-]-7,8-dihydro-6H-indeno[4,5-d]-1,3-dioxole-2,2-dicarboxylic acid diisopropyl ester.

14. A method as defined in claim 1 wherein the optically active compound is (R,R)-7-[[2-(3-chlorophenyl)-2-hydroxyethyl]amino]-7,8-dihydro-6H-indeno[5,6-d]-1,3-dioxole-2,2-dicarboxylic acid disodium salt.

15. A method as defined in claim 1 wherein the racemic compound is (R*,R*)-6-[[2-(3-chlorophenyl)-2-hydroxyethyl]amino]-5,6,7,8-tetrahydronaphtho[2,3-d]-1,3-dioxole-2,2-dicarboxylic acid disodium salt.

16. A method as defined in claim 1 wherein the racemic compound is (R*,S*)-6-[[2-(3-chlorophenyl)-2-hydroxyethyl]amino]-5,6,7,8-tetrahydronaphtho[2,3-d]-1,3-dioxole-2,2-dicarboxylic acid disodium salt.

17. A method of treating obesity in mammals which comprises administering to an obese patient an antiobesity effective amount of a compound of the formula:

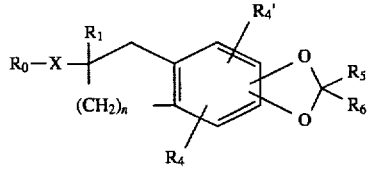

wherein:

$R_o$ is naphthyl, 5,6,7,8-tetrahydronaphth-(1 or 2)-yl, 5,8-dihydronaphth-(1 or 2)-yl; or

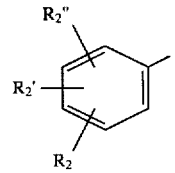

and $R_2$, $R_{2'}$, $R_{2''}$ may be the same or different and are hydrogen, $(C_1-C_4)$ alkyl, $(C_1-C_4)$ alkoxy, hydroxy, halogen (chlorine, bromine, fluorine or iodine), trifluoromethyl, carboxy, hydroxy$(C_1-C_{10})$ alkyl, $(C_1-C_{10})$-alkoxycarbonyl or thio$(C_1-C_4)$alkyl; n is an integer from 1 to 3;

X is the divalent radical:

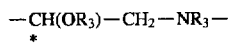

wherein $R_3$ is hydrogen, $(C_1-C_4)$alkyl, $(C_1-C_4)$acyl, $(C_1-C_4)$alkoxycarbonyl or benzoyl; and wherein * denotes an asymmetric carbon;

$R_1$ is hydrogen or $(C_1-C_4)$alkyl; $R_4$ and $R_{4'}$ may be the same or different and are hydrogen, $(C_1-C_4)$ alkyl, $(C_1-C_4)$alkoxy, hydroxy, halogen (chloride, bromine, fluorine or iodine), trifluoromethyl, carboxy, hydroxy$(C_1-C_{10})$alkyl, $(C_1-C_{10})$alkoxycarbonyl or thio$(C_1-C_4)$alkyl;

$R_5$ and $R_6$ hydrogen, carboxyl, $(C_1-C_{10})$alkoxycarbonyl, hydroxymethyl, $-CH_2OCH_2COOR_7$ or $-CH_2OCH_2CH_2OR_7$, wherein $R_7$ is hydrogen, or $(C_1-C_4)$alkyl, or $CONHR_8$, $R_8$ is hydrogen, straight or branched $(C_1-C_{10})$alkyl or 2-methoxy-1-ethyl; with the proviso that $R_5$ and $R_6$ may not both be hydrogen; and the pharmacologically acceptable salt or ester thereof; the racemic mixture thereof or the stereoisomeric mixture thereof.

18. A method as defined in claim 17 wherein $R_1$ is hydrogen, n is an integer of 1 or 2, and $R_5$ and $R_6$ are the same and are carboxy, $(C_1-C_{10})$alkoxycarbonyl or alkali metal carboxylate.

19. A method as defined in claim 17 wherein $R_4$ and $R_{4'}$ are hydrogen.

20. A method as defined in claim 17 wherein $R_2$ is $(C_1-C_4)$alkyl, $(C_1-C_4)$alkoxy, hydroxy, halogen, (chlorine, bromine, fluorine or iodine), trifluoromethyl, carboxy, hydroxy$(C_1-C_{10})$alkyl, $(C_1-C_{10})$alkoxycarbonyl, or thio$(C_1-C_4)$alkyl; and $R_{2'}$ and $R_{2''}$ are hydrogen.

21. A method as defined in claim 19 wherein $R_2$ is a chloro substituent.

22. A method according to claim 20, wherein $R_1$, $R_4$ and $R_{4'}$ are hydrogen.

23. A method according to claim 21 wherein $R_5$ and $R_6$ are carboxy.

24. A method according to claim 21 wherein $R_5$ and $R_6$ are $-CO_2CH(CH_3)_2$.

25. A method as defined in claim 24 wherein $R_2$ is a chloro substituent at the 3 position.

26. A method as defined in claim 21 wherein $R_5$ and $R_6$ are $-CO_2^-$ $Na^+$.

27. A method as defined in claim 17 wherein the compound is a racemic compound according which is (R*,S*)-

6[[2-(3-chlorophenyl)-2-hydroxyethyl]amino]-5,6,7,8-tetrahydronaphtho[1,2-d]-1,3-dioxole-2,2-dicarboxylic acid disodium salt.

28. A method as defined in claim 17 wherein the compound is an optically active compound which is (R,R)-7-[[2-(3-chlorophenyl)-2-hydroxyethyl]amino]-7,8-dihydro-6H-indeno[4,5-d]-1,3-dioxole-2,2-dicarboxylic acid, disodium salt.

29. A method as defined in claim 17 wherein the compound is an optically active compound which is (R,R)-7-[[2-(3-chlorophenyl)-2-hydroxyethyl]amino]-7,8-dihydro-6H-indeno[4,5-d]-1,3-dioxole-2,2-dicarboxylic acid diisopropyl ester.

30. A method as defined in claim 17 wherein the optically active compound is (R,R)-7-[[2-(3-chlorophenyl)-2-hydroxyethyl]amino]-7,8-dihydro-6H-indeno[5,6-d]-1,3-dioxole-2,2-dicarboxylic acid disodium salt.

31. A method as defined in claim 17 wherein the racemic compound is (R*,R*)-6-[[2-(3-chlorophenyl)-2-hydroxyethyl]amino]-5,6,7,8-tetrahydronaphtho[2,3-d]-1,3-dioxole-2,2-dicarboxylic acid disodium salt.

32. A method as defined in claim 17 wherein the racemic compound is (R*,S*)-6-[[2-(3-chlorophenyl)-2-hydroxyethyl]amino]-5,6,7,8-tetrahydronaphtho[2,3-d]-1,3-dioxole-2,2-dicarboxylic acid disodium salt.

33. A method of treating diabetes in mammals which comprises administering to a diabetic patient an antidiabetic effective amount of a compound of the formula:

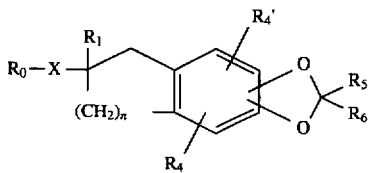

wherein:

$R_o$ is naphthyl, 5,6,7,8-tetrahydronaphth-(1 or 2)-yl, 5,8-dihydronaphth-(1 or 2)-yl; or

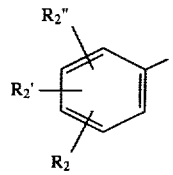

and $R_2$, $R_2'$, $R_2''$ may be the same or different and are hydrogen, $(C_1-C_4)$ alkyl, $(C_1-C_4)$ alkoxy, hydroxy, halogen (chlorine, bromine, fluorine or iodine), trifluoromethyl, carboxy, hydroxy$(C_1-C_{10})$ alkyl, $(C_1-C_{10})$-alkoxycarbonyl or thio$(C_1-C_4)$alkyl; n is an integer from 1 to 3;

X is the divalent radical:

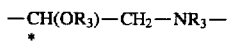

wherein $R_3$ is hydrogen, $(C_1-C_4)$alkyl, $(C_1-C_4)$acyl, $(C_1-C_4)$alkoxycarbonyl or benzoyl; and wherein * denotes an asymmetric carbon;

$R_1$ is hydrogen or $(C_1-C_4)$alkyl; $R_4$ and $R_4'$ may be the same or different and are hydrogen, $(C_1-C_4)$ alkyl, $(C_1-C_4)$alkoxy, hydroxy, halogen (chloride, bromine, fluorine or iodine), trifluoromethyl, carboxy, hydroxy$(C_1-C_{10})$alkyl, $(C_1-C_{10})$alkoxycarbonyl or thio$(C_1-C_4)$alkyl;

$R_5$ and $R_6$ hydrogen, carboxyl, $(C_1-C_{10})$alkoxycarbonyl, hydroxymethyl, —$CH_2OCH_2COOR_7$ or —$CH_2OCH_2CH_2OR_7$, wherein $R_7$ is hydrogen, or $(C_1-C_4)$alkyl, or $CONHR_8$, $R_8$ is hydrogen, straight or branched $(C_1-C_{10})$alkyl or 2-methoxy-1-ethyl; with the proviso that $R_5$ and $R_6$ may not both be hydrogen; and the pharmacologically acceptable salt or ester thereof; the racemic mixture thereof or the stereoisomeric mixture thereof.

34. A method as defined in claim 33 wherein $R_1$ is hydrogen, n is an integer of 1 or 2, and $R_5$ and $R_6$ are the same and are carboxy, $(C_1-C_{10})$alkoxycarbonyl or alkali metal carboxylate.

35. A method as defined in claim 33 wherein $R_4$ and $R_4'$ are hydrogen.

36. A method as defined in claim 33 wherein $R_2$ is $(C_1-C_4)$alkyl, $(C_1-C_4)$alkoxy, hydroxy, halogen, (chlorine, bromine, fluorine or iodine), trifluoromethyl, carboxy, hydroxy$(C_1-C_{10})$alkyl, $(C_1-C_{10})$alkoxycarbonyl, or thio$(C_1-C_4)$alkyl; and $R_2'$ and $R_2''$ are hydrogen.

37. A method as defined in claim 36 wherein $R_2$ is a chloro substituent.

38. A method according to claim 37, wherein $R_1$, $R_4$ and $R_4'$ are hydrogen.

39. A method according to claim 37 wherein $R_5$ and $R_6$ are carboxy.

40. A method according to claim 37 wherein $R_5$ and $R_6$ are —$CO_2CH(CH_3)_2$.

41. A method as defined in claim 40 wherein $R_2$ is a chloro substituent at the 3 position.

42. A method as defined in claim 40 wherein $R_5$ and $R_6$ are —$CO_2^{31}$ $Na^+$.

43. A method as defined in claim 33 wherein the compound is a racemic compound according which is (R*,S*)-6[[2-(3-chlorophenyl)-2-hydroxyethyl]amino]-5,6,7,8-tetrahydronaphtho[1,2-d]-1,3-dioxole-2,2-dicarboxylic acid disodium salt.

44. A method as defined in claim 33 wherein the compound is an optically active compound which is (R,R)-7-[[2-(3-chlorophenyl)-2-hydroxyethyl]amino]-7,8-dihydro-6H-indeno[4,5-d]-1,3-dioxole-2,2-dicarboxylic acid, disodium salt.

45. A method as defined in claim 33 wherein the compound is an optically active compound which is (R,R)-7-[[2-(3-chlorophenyl)-2-hydroxyethyl]amino]-7,8-dihydro-6H-indeno[4,5-d]-1,3-dioxole-2,2-dicarboxylic acid diisopropyl ester.

46. A method as defined in claim 33 wherein the optically active compound is (R,R)-7-[[2-(3-chlorophenyl)-2-hydroxyethyl]amino]-7,8-dihydro-6H-indeno[5,6-d]-1,3-dioxole-2,2-dicarboxylic acid disodium salt.

47. A method as defined in claim 33 wherein the racemic compound is (R*,R*)-6-[[2-(3-chlorophenyl)-2-hydroxyethyl]amino]-5,6,7,8-tetrahydronaphtho[2,3-d]-1,3-dioxole-2,2-dicarboxylic acid disodium salt.

48. A method as defined in claim 33 wherein the racemic compound is (R*,S*)-6-[[2-(3-chlorophenyl)-2-hydroxyethyl]amino]-5,6,7,8-tetrahydronaphtho[2,3-d]-1,3-dioxole-2,2-dicarboxylic acid disodium salt.

* * * * *